(12) United States Patent
Nicholson et al.

(10) Patent No.: US 9,552,898 B2
(45) Date of Patent: *Jan. 24, 2017

(54) SYSTEMS AND METHODS FOR OBTAINING AND DISPLAYING AN X-RAY IMAGE

(71) Applicant: General Electric Company, Schenectady, NY (US)

(72) Inventors: Bret David Nicholson, Tooele, UT (US); David Barker, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 179 days.

This patent is subject to a terminal disclaimer.

(21) Appl. No.: 14/518,866

(22) Filed: Oct. 20, 2014

(65) Prior Publication Data

US 2016/0109386 A1    Apr. 21, 2016

Related U.S. Application Data

(63) Continuation of application No. 13/413,117, filed on Mar. 29, 2012, now Pat. No. 8,942,346.

(51) Int. Cl.
| | |
|---|---|
| *G21K 1/02* | (2006.01) |
| *G21K 1/00* | (2006.01) |
| *A61B 6/06* | (2006.01) |
| *G06T 3/60* | (2006.01) |
| *A61B 6/00* | (2006.01) |
| *G21K 1/04* | (2006.01) |

(52) U.S. Cl.
CPC . *G21K 1/02* (2013.01); *A61B 6/06* (2013.01); *A61B 6/4441* (2013.01); *A61B 6/461* (2013.01); *G01N 2223/316* (2013.01); *G06T 3/60* (2013.01); *G21K 1/00* (2013.01); *G21K 1/04* (2013.01)

(58) Field of Classification Search
CPC .......... H05G 1/64; G01N 23/083; G21K 1/00; G21K 1/02; G06T 1/00; G06T 1/0007; G06T 3/00; G06T 3/60
USPC ... 378/62, 91, 98, 98.2, 98.8, 145, 147, 204, 378/210, 901; 382/128, 131, 132, 276, 382/293, 296, 297

See application file for complete search history.

(56) References Cited

U.S. PATENT DOCUMENTS

| | | |
|---|---|---|
| 4,093,864 A | 6/1978 | Hahn et al. |
| 4,514,859 A | 4/1985 | Holzermer |

(Continued)

FOREIGN PATENT DOCUMENTS

WO      2010092516 A1    8/2010

*Primary Examiner* — Anastasia Midkiff

(57) ABSTRACT

Systems and methods for obtaining and displaying a collimated X-ray image are described. The methods can include providing an X-ray device having an X-ray source, a square or rectangular X-ray detector, and a collimator. The collimator can be sized and shaped to collimate an X-ray beam from the X-ray source that exposes a receptor region on the detector. The collimator can allow the X-ray image received by the X-ray detector to have any suitable shape that allows a relatively large view of the image to be displayed and rotated on the display device without changing the shape or size of the image as it rotated. In some instances, the collimator provides the image with superellipse shapes or cornerless shapes having four substantially straight edges with a 90 degree corner missing between at least two edges that run substantially perpendicular to each other. Other embodiments are described.

5 Claims, 13 Drawing Sheets

(56) References Cited

U.S. PATENT DOCUMENTS

| | | |
|---|---|---|
| 6,542,573 B2 | 4/2003 | Schomberg |
| 8,942,346 B2 * | 1/2015 | Nicholson ................ A61B 6/06 |
| | | 378/147 |
| 2004/0264646 A1 | 12/2004 | Spahn |
| 2010/0270480 A1 | 10/2010 | Echner |

* cited by examiner

SYSTEMS AND METHODS FOR OBTAINING AND DISPLAYING AN X-RAY IMAGE

CROSS-REFERENCE TO RELATED APPLICATION

The present application is a continuation application of U.S. Pat. No. 8,942,346, issued on, Jan. 27, 2015, the entire disclosure of which is hereby incorporated by reference.

FIELD

This application relates generally to systems and methods for obtaining and displaying an X-ray image. In particular, this application relates to systems and methods for using an X-ray collimator to generate an X-ray image in which one or more corners of an X-ray detector that is used to capture the image are not displayed as part of the image. In this manner, a relatively large view of the image can be displayed and rotated on a square or rectangular display device without changing the image's shape or size as the image is rotated.

BACKGROUND

A typical X-ray imaging system comprises an X-ray source and an X-ray detector. The X-rays that are emitted from the X-ray source can impinge on the X-ray detector and provide an X-ray image of the object (or objects) that are placed between the X-ray source and the X-ray detector. In one type of X-ray imaging system, a fluoroscopic imaging system, the X-ray detector is often an image intensifier or, more recently, a flat panel digital detector.

In many medical imaging applications, a collimator is placed between the X-ray source and the X-ray detector to limit the size and shape of the field of the X-ray beam. The collimator can shape or limit the X-ray beam to an area of a patient's body that requires imaging, preventing unnecessary X-ray exposure to areas surrounding the body part that is being imaged and protecting the patient from needless X-ray exposure. And because the collimator can limit the X-rays impinging on the X-ray detector near the body part being imaged, the collimator helps improve image contrast and quality. For example, the collimator can reduce excess X-rays from impinging on a flat panel digital detector, reducing or preventing image blooming or bleeding (which tend to occur when the detector is overloaded with X-rays). Thus, some conventional collimators can minimize X-ray exposure and maximize the efficiency of the X-ray dosage to obtain an optimum amount of data for diagnosis.

SUMMARY

This application relates to systems and methods for obtaining and displaying a collimated X-ray image. The methods can include providing an X-ray device having an X-ray source, a square or rectangular X-ray detector, and a collimator. The collimator can be sized and shaped to collimate an X-ray beam from the X-ray source that exposes a receptor region on the detector. The collimator can allow the X-ray image received by the X-ray detector to have any suitable shape that allows a relatively large view of the image to be displayed and rotated on the display device without changing the shape or size of the image as it rotated. In some instances, the collimator provides the image with superellipse shapes or cornerless shapes having four substantially straight edges with a 90 degree corner missing between at least two edges that run substantially perpendicular to each other (e.g., a squircle, a rounded square, rounded rectangle, a chamfered square, chamfered rectangle, etc.).

BRIEF DESCRIPTION OF THE DRAWINGS

The following description can be better understood in light of the Figures, in which.

Figure 1:
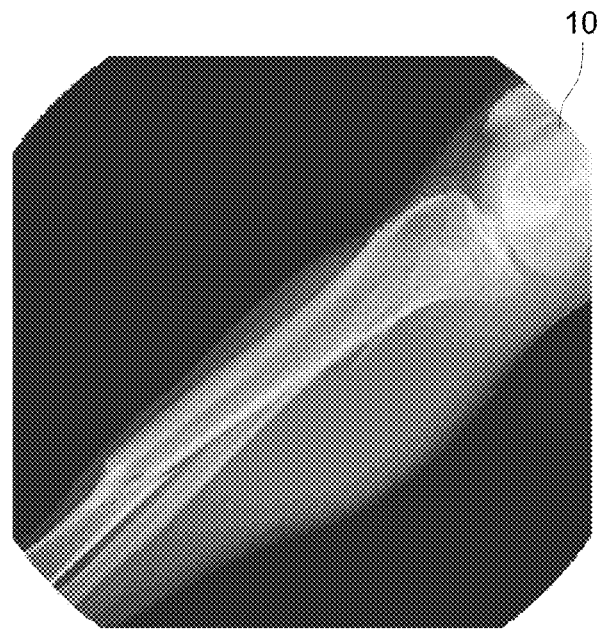
FIG. 1 shows some embodiments of a collimated X-ray image.

The Figures illustrate specific aspects of the systems and methods for displaying collimated X-ray images. Together with the following description, the Figures demonstrate and explain the principles of the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices. Moreover, for clarity, the Figures may show simplified or partial views, and the dimensions of elements in the Figures may be exaggerated or otherwise not in proportion.

DETAILED DESCRIPTION

The following description supplies specific details in order to provide a thorough understanding. Nevertheless, the skilled artisan would understand that the described systems and methods for obtaining and displaying collimated X-ray images can be implemented and used without employing these specific details. Indeed, the described systems and methods can be placed into practice by modifying the illustrated devices and methods and can be used in conjunction with any other apparatus and techniques conventionally used in the industry. For example, while the description below focuses on systems and methods for displaying collimated X-ray images that were created using a fluoroscopic X-ray device that obtains X-ray images in near real time, the described systems and methods (or portions thereof) can be used with any other suitable device or technique. For instance, the described systems and methods (or portions thereof) may be used with X-ray devices that produce traditional, plain X-ray images; with X-ray treatment procedures used in radiation therapy; in procedures for collimating gamma radiation; in nuclear medicine; and/or for a combination of different imaging and/or treatment techniques.

As the terms on, attached to, connected to, or coupled to are used herein, one object (e.g., a material, an element, a structure, etc.) can be on, attached to, connected to, or coupled to another object, regardless of whether the one object is directly on, attached, connected, or coupled to the other object or whether there are one or more intervening objects between the one object and the other object. Also, directions (e.g., on top of, below, above, top, bottom, side, up, down, under, over, upper, lower, horizontal, vertical, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more. Additionally, the terms X-ray image, image, collimated image, and collimated X-ray image may refer to an X-ray image that is produced from a portion of an X-ray detector that is exposed to an X-ray beam that has been collimated with a collimator.

As used herein, in some embodiments the term square may refer to a shape with four sides of equal length that also has four 90 degree corners. The term circle, in some embodiments, may refer to a closed plane curve having all points at a given distance from a common center point. The term squircle, in some embodiments, may refer to a Boolean intersection of a concentric circle and square, where the final shape has an area less than either the circle or the square. The term squircle, in other embodiments, may refer to a Boolean intersection of a square and a concentric circle whose diameter is greater than the length of the side of the square, but less than the diagonal of the square. The term mathematical squircle, in some embodiments, may refer to a specific type of superellipse with a shape between those of a concentric square and circle and may be expressed as a quadric planar curve or as a quadric Cartesian equation. A mathematical squircle, as opposed to the squircle shapes immediately above, maintains the tangent continuity between the circular corners with the flatter edges of a superellipse. The terms rounded square and rounded rectangle, in some embodiments, may respectively refer to a square or a rectangle with fillets breaking the corners (e.g., circular corners that are tangent to the edges of the square or rectangle). Additionally, in some embodiments the terms chamfered square and chamfered rectangle may respectively refer to a square and rectangle having any number of chamfers breaking their corners.

As mentioned above, this application describes systems and methods for displaying collimated X-ray images. In some embodiments, the described systems and methods use a collimator to prevent an X-ray beam from impinging on one or more corners of an X-ray detector. The collimator can provide the image with any suitable shape that allows one or more corners of the X-ray detector that is used to obtain the image not to be displayed in the image. In some instances, the X-ray image has a perimeter with a (i) a superellipse shape and (ii) a cornerless shape with at least two substantially straight edges that run substantially perpendicular to each other, wherein such edges do not physically intersect with each other at a 90-degree corner.

Some embodiments of a collimated image 10 are shown in FIG. 1. By having any of the described shapes, the collimated image can be shown on a relatively large portion of a display area of a display device (e.g., a square or rectangular monitor, screen, projector, TV, etc.), and the entire image can be viewed as it is rotated about its center, without requiring the image to be reshaped or resized. Thus, the described collimated image can maintain its size and geometry during rotation on the display device, while maximizing its on-screen, image size and the amount of the receptor area of the X-ray detector that is used to take the image.

Figure 2:
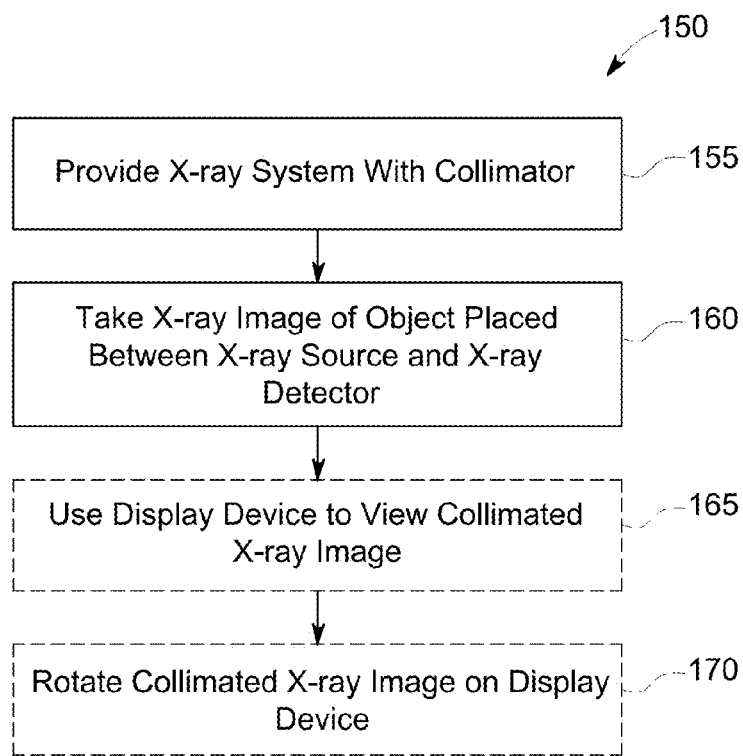
FIG. 2 shows some embodiments of a method for displaying the collimated X-ray image.

FIG. 2 shows some embodiments of a method 150 for displaying the described collimated X-ray images. Although this method can be modified in any suitable manner (including by rearranging, adding to, removing, modifying, substituting, and otherwise modifying various portions of the method), FIG. 2 shows those embodiments in which the method begins at 155 by providing an X-ray system 15.

The X-ray system 15 can comprise any suitable X-ray device that is capable of capturing the described X-ray images 10. For example, the X-ray system can comprise a mobile X-ray device (e.g., an X-ray device comprising a C-arm, a mini C-arm, an O-arm, a non-circular arm, etc.), and a fixed X-ray device. By way of illustration, FIG. 3 shows an X-ray imaging system 15 comprises that a C-arm X-ray device 18.

The X-ray system 15 can also comprise any component that allows it to take the collimated X-ray images 10. In some embodiments, FIG. 3 shows the X-ray imaging system 15 comprises an X-ray source 20, an X-ray detector 25, and a collimator 30. Any suitable X-ray source can be used, including a standard X-ray source, a rotating anode X-ray source, a stationary or fixed anode X-ray source, a solid state X-ray emission source, or a fluoroscopic X-ray source 35 (as shown in FIG. 3). Any suitable X-ray detector can be used, such as an image intensifier or a flat panel digital detector 40 (as shown in FIG. 3). Indeed, in some embodiments, the X-ray detector comprises a square or a rectangular flat panel detector.

Figure 3:
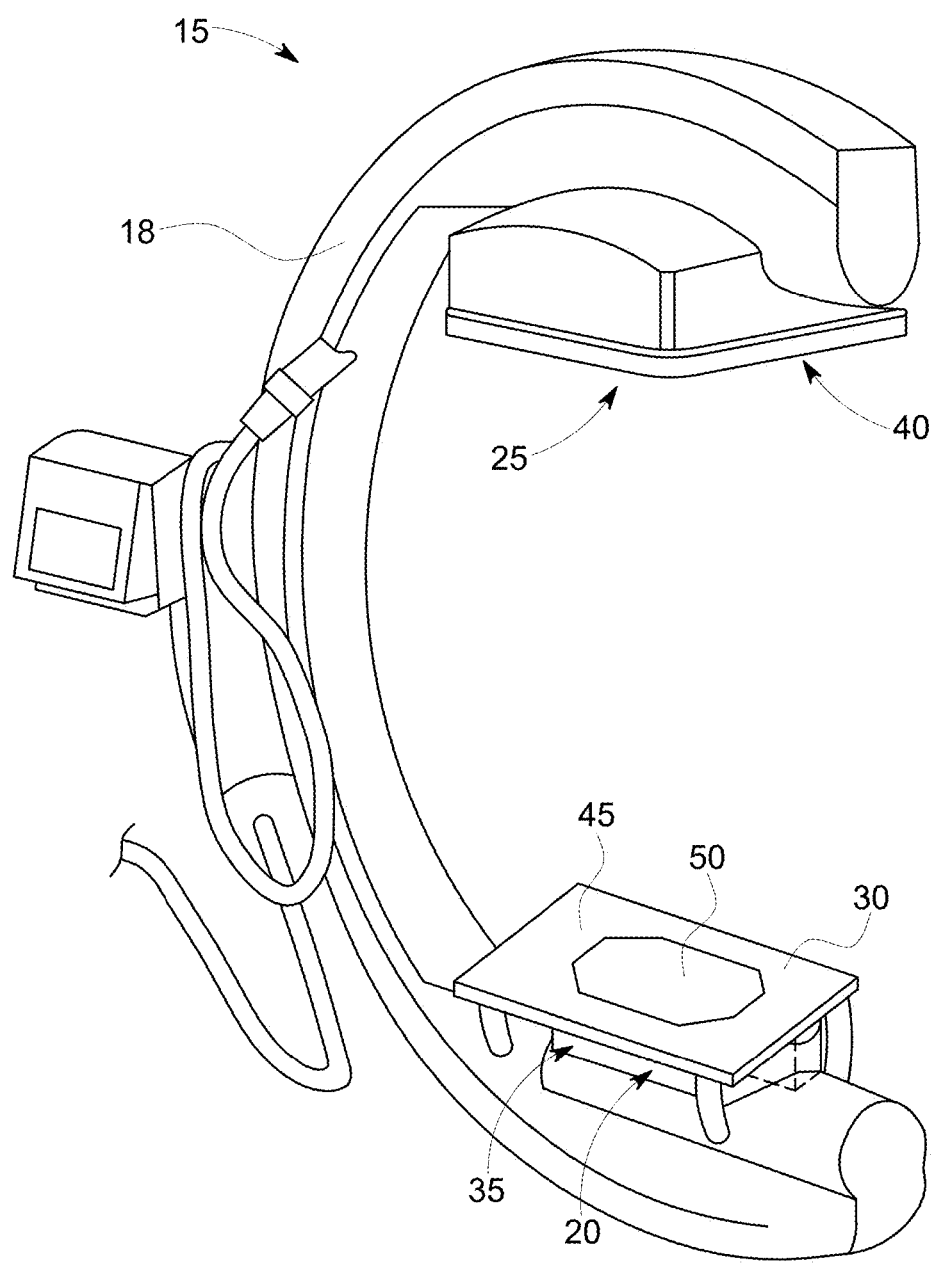
FIG. 3 shows a side view of a representative embodiment of an X-ray imaging system comprising some embodiments a collimator.

FIG. 3 shows some embodiments in which the collimator 30 comprises an X-ray attenuating material 45 that defines an aperture 50. The collimator 30 can comprise any suitable X-ray attenuating material 45 that allows it to collimate an X-ray beam. Some examples of suitable X-ray attenuating materials include tungsten, lead, gold, copper, tungsten-impregnated substrates (e.g., glass or a polymer impregnated with tungsten), coated substrates (e.g., glass or a polymer coated with tungsten, lead, gold, etc.), steel, aluminum, bronze, brass, rare earth metals, or combinations thereof. In some embodiments, however, the collimator comprises tungsten.

The collimator 30 collimates an X-ray beam (not shown) so that a resultant image 10 comprises any suitable shape that does not include one or more corners of the X-ray detector 40 that is used to obtain the image. In some embodiments, however, the collimator provides the image with a shape corresponding to a shape of the aperture, wherein the image shape is a superellipse shape or a cornerless shape. A cornerless shape comprises a shape missing one or more 90 degree corners (i.e., two edges that run substantially perpendicular to each other without containing a 90 degree corner between those edges). The cornerless shape may contain corners with a degree less than 90 degrees. Some examples of such shapes include a rounded square, a rounded rectangle, a chamfered square, a chamfered rectangular, a rectangle with curved borders, a truncated circle, an octagon, a hexagon, or any other suitable shape.

Where the aperture 50 has the shape of a superellipse, it can have any suitable characteristic that allows the shape of the aperture to be classified as a superellipse (as described above) and that allows the collimator 30 to prevent the X-ray beam from impinging on the corners of the X-ray detector 40. By way of example, the aperture can be a shape that is generated by a formula selected from: (i) $(x-a)^4+(y-b)^4=r^4$, (ii) $|x-a|^n+|y-b|^n=|r|^n$, and $$\left|\frac{(x-a)}{r_a}\right|^n + \left|\frac{(y-b)}{r_b}\right|^n \qquad \text{(iii)}$$

wherein a, b is the center point; r is the minor; n is equal to 4; and $r_a$ and $r_b$ are the semi-major and semi-minor axes, respectively.

Figure 4:
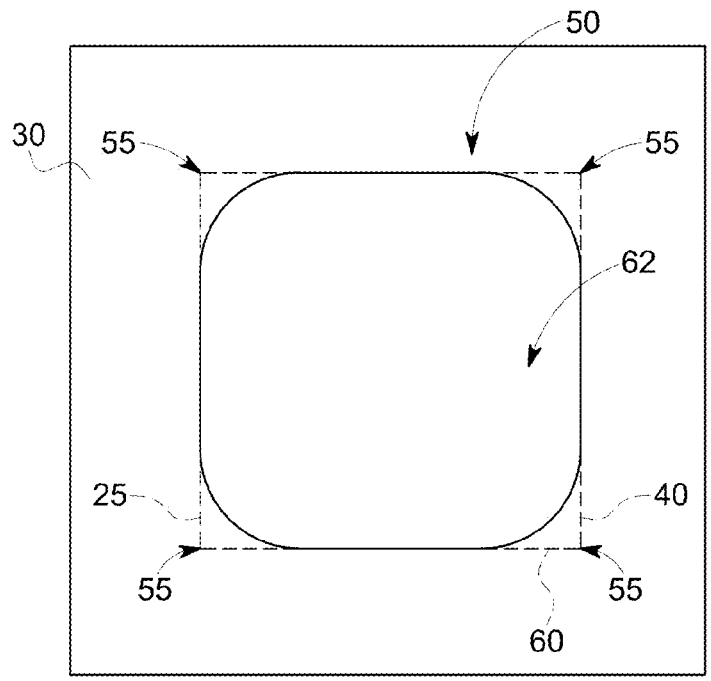
FIGS. 4, 6, 8, 10, and 12 each show a top schematic view of the some embodiments of the collimator that are intended to be used with the flat panel digital detector.

FIG. 4 shows some embodiments in which the collimator 30 defines an aperture that has a shape of a superellipse. Furthermore, FIG. 4 shows the aperture is sized so that a portion of the collimator 30 overlaps (and thereby collimates) the corners 55 of a corresponding square X-ray detector 25 (e.g., a flat panel detector 40), wherein the perimeter 60 of a receptor area 62 of the detector 25 is illustrated by a dotted line.

Figure 5:
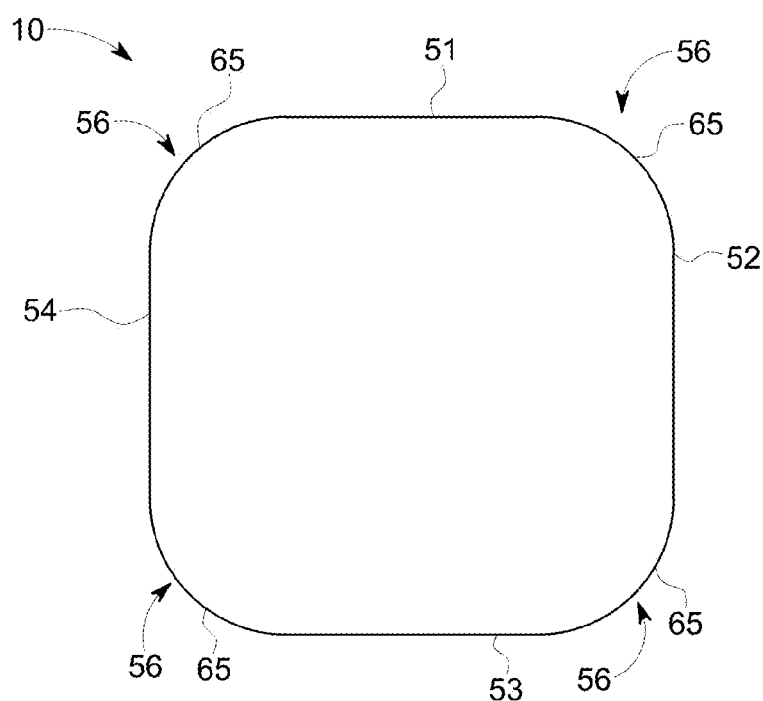
FIGS. 5, 7, 9, 11, and 13 each show a top view of some embodiments of the collimated image taken from the setups of FIGS. 4, 6, 8, 10, and 12, respectively.
Figure 6:
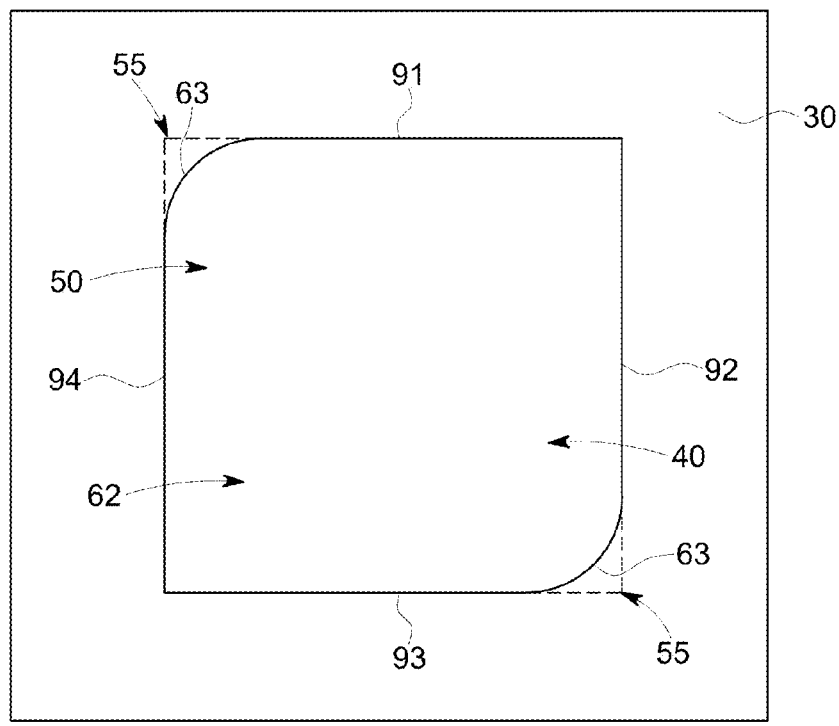
Figure 7:
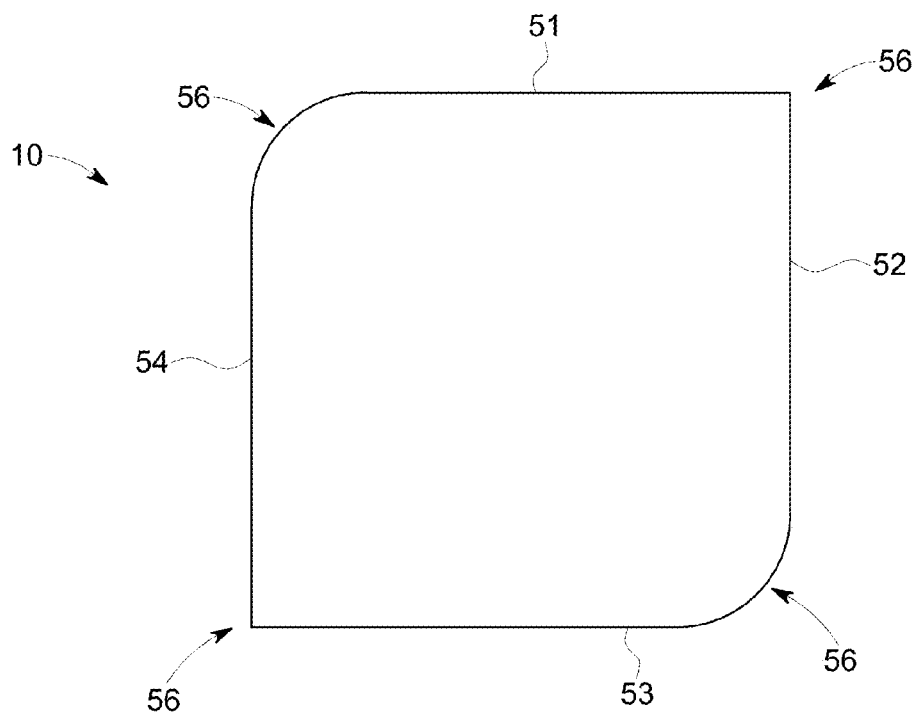
Figure 8:
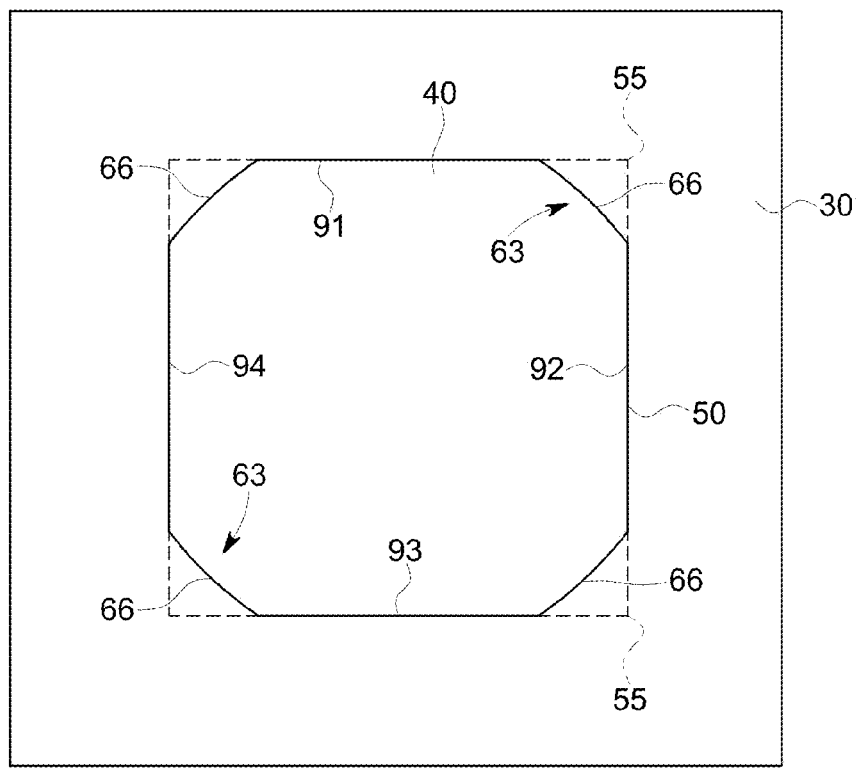
Figure 9:
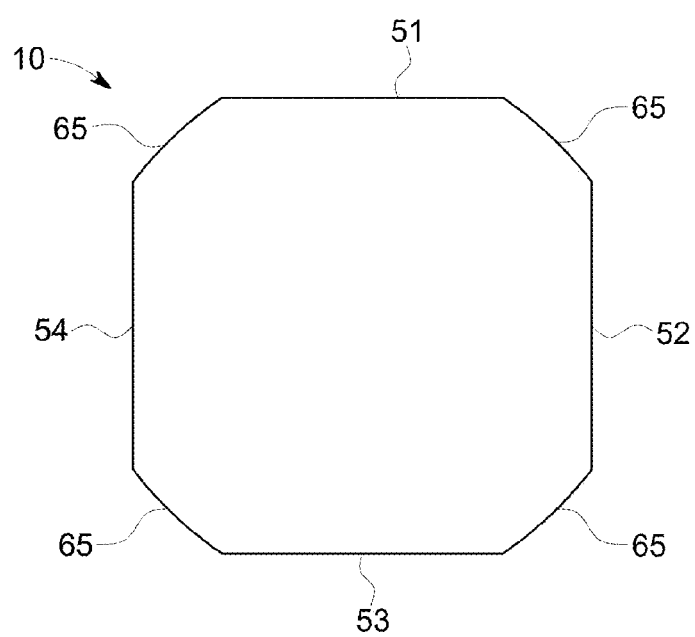
Figure 10:
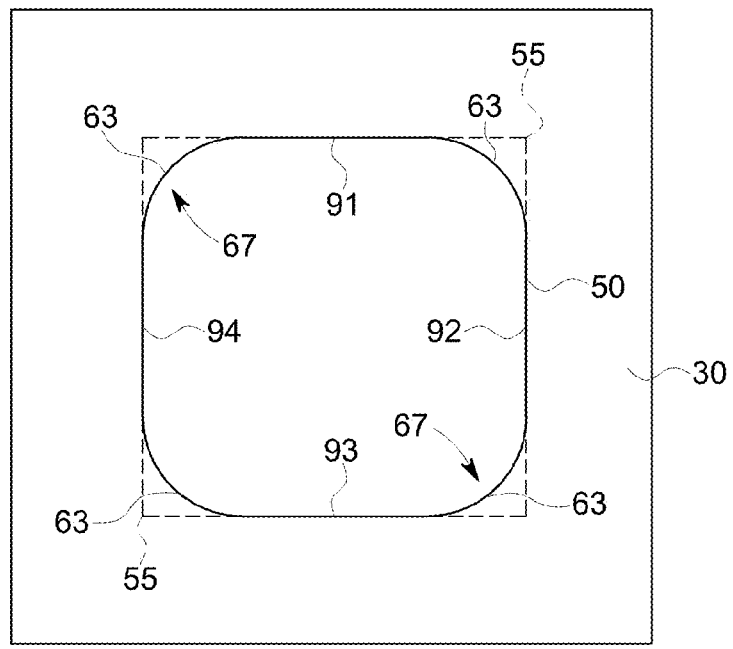
Figure 11:
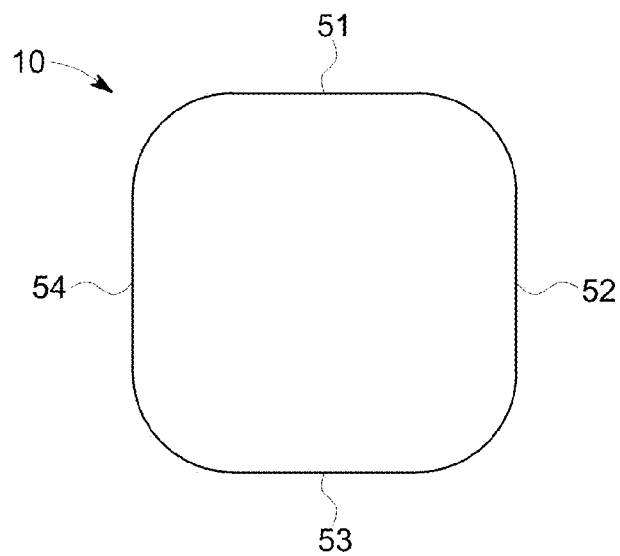
Figure 12:
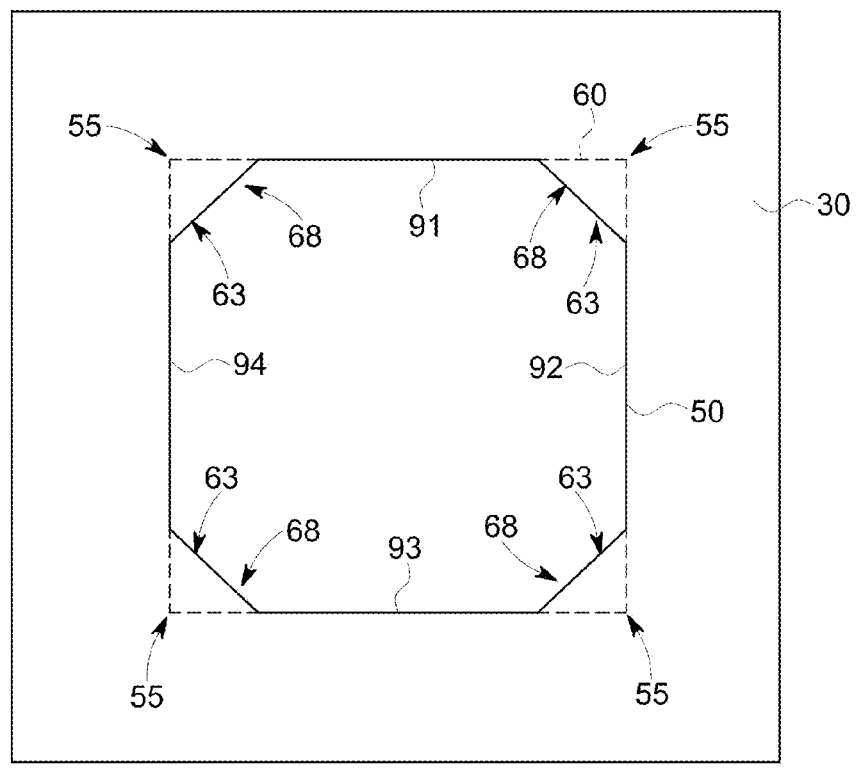
Figure 13:
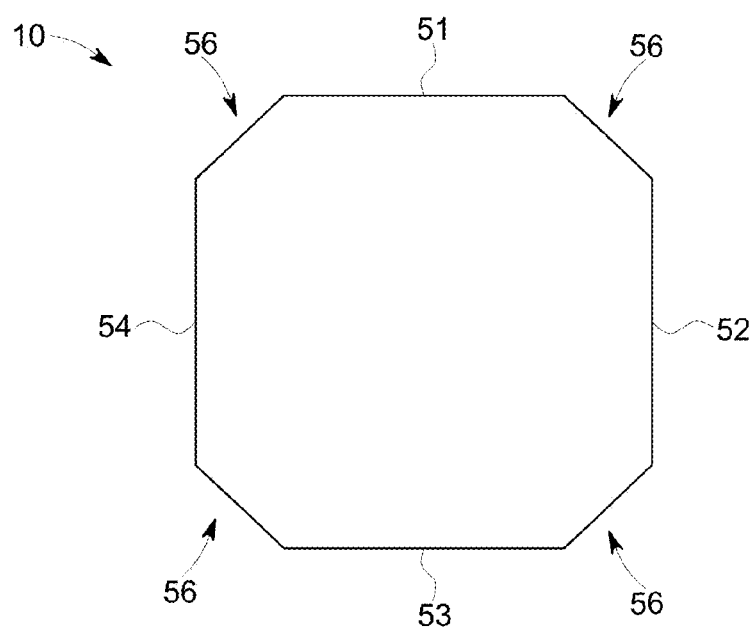

FIG. 5 shows one example of a collimated image 10 that has been taken with the collimator 30 of FIG. 4. In particular, FIG. 5 shows that image 10 has a shape of a superellipse, in which a first 51 and second 52 images edge, a second 52 and third 53 image edge, a third 53 and fourth 54 edge, and a fourth 54 and first 51 image edge, respectively, do not physically intersect at a 90 degree corner. Instead, FIG. 5 shows the image's corners 56 are trimmed (or collimated) so the image's first edge 51 and third edge 53 are each separated from the image's second edge 52 and fourth edge 54 by a non-linear (i.e., substantially curved) image border 65.

Where the aperture 50 comprises the cornerless shape, the aperture can have any suitable characteristic that allows it to function as intended. In one example, FIG. 6 shows the aperture 50 comprises a first 91 and third 93 aperture edge, which run substantially parallel to each other, and which run substantially perpendicular to both a second 92 and a fourth 94 aperture edge. In another example, FIG. 6 shows that instead of physically intersecting at a 90 degree corner, one or more corresponding aperture edges that run perpendicular to each other (e.g., the second 92 and third 93 aperture edges) can be attached to each other with a border 63 that allows the collimator 30 to shield a 90 degree corner 55 of a corresponding detector 40. Additionally, while this disclosure focuses on using an aperture in which all of the apertures edges are substantially equal in length (e.g., an aperture having the appearance of a trimmed square), the skilled artisan will recognize that the aperture could be modified so that any two edges running parallel to each other may be longer or shorter than the other edges of the aperture (e.g., the aperture could have the appearance of a rectangle with trimmed corners).

Where the aperture 50 comprises one of the described cornerless shapes, the aperture can be missing any suitable number of corners (e.g., one or more corners of the aperture can be filled in with an X-ray attenuating material), including 1, 2, 3, 4, or more. Indeed, FIG. 6 shows configurations where a portion of the collimator 30 shields two corners 55 (located diagonally from each other) of the X-ray detector's receptor area 62. Accordingly, FIG. 7 shows that an image 10 captured with the configuration of FIG. 6 contains two corners 56 that lack a 90 degree corner between two perpendicular edges of the image (e.g., between the image's second 52 and third 53 edges and between the image's first 51 and fourth 54 edges).

Where the aperture 50 is missing one or more corners (e.g., contains an X-ray attenuating material that prevents the X-ray beam from impinging on one or more corners of a corresponding X-ray detector 40), the collimator can collimate the X-ray beam so that the resultant image 10 has any suitably shaped border 63 between adjacent aperture edges that run perpendicular to each other. Some examples of suitable borders include a border with the shape of an arc of a circle, a chamfered border, a rounded border, a convex border, a concave border, a zigzagged border, a curved border, an irregular border, etc. In this regard, FIG. 8 shows that in some embodiments in which all four borders 63 of the aperture 50 (and therefore borders of the image 63) comprise an arc-shaped border 66, the aperture 50 defines a squircle. FIG. 10 shows some configurations in which the each of the aperture's four borders 63 comprises a rounded border 67, the aperture 50 can comprise rounded square (or rectangle where applicable). Additionally, FIG. 12 shows some embodiments in which each of the aperture's four borders 63 comprises a chamfered border 68, the aperture 50 comprises a chamfered square (or rectangle where applicable). Images with shapes corresponding to the collimators 30 of FIGS. 8, 10, and 12 are respectively shown in FIGS. 9, 11, and 13.

Figure 14:
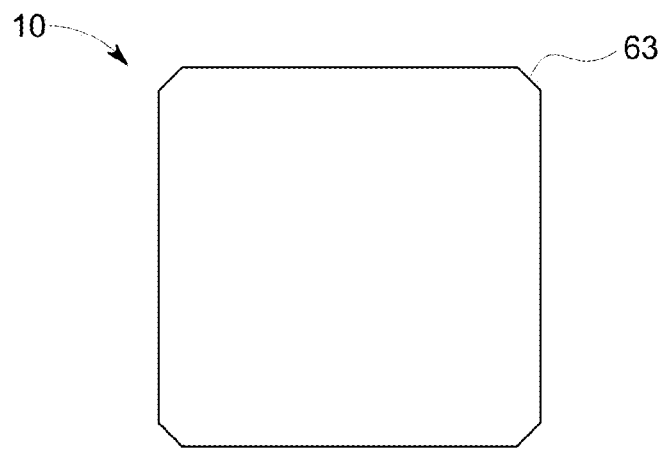
FIGS. 14-16 each show a top view of embodiments of the collimated image in which the image comprises a squircle.
Figure 15:
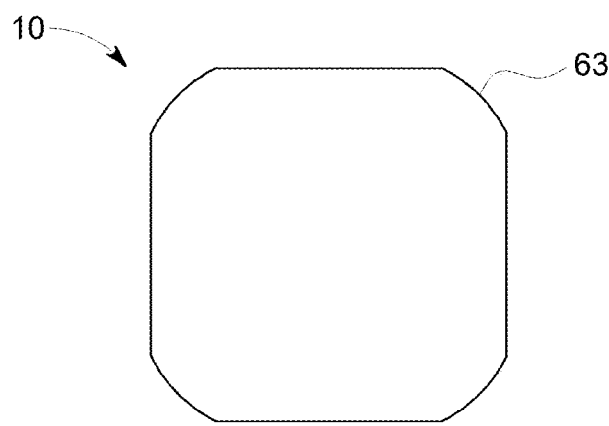
Figure 16:
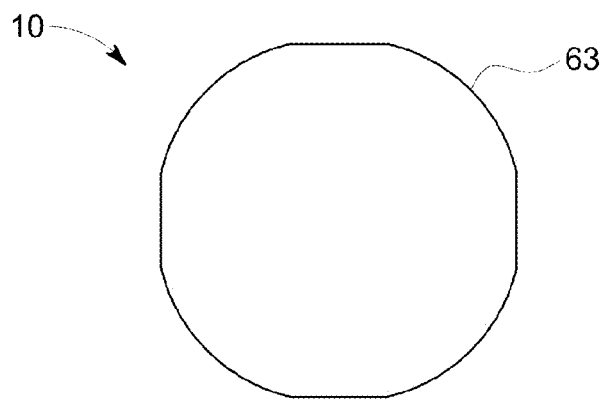
Figure 17:
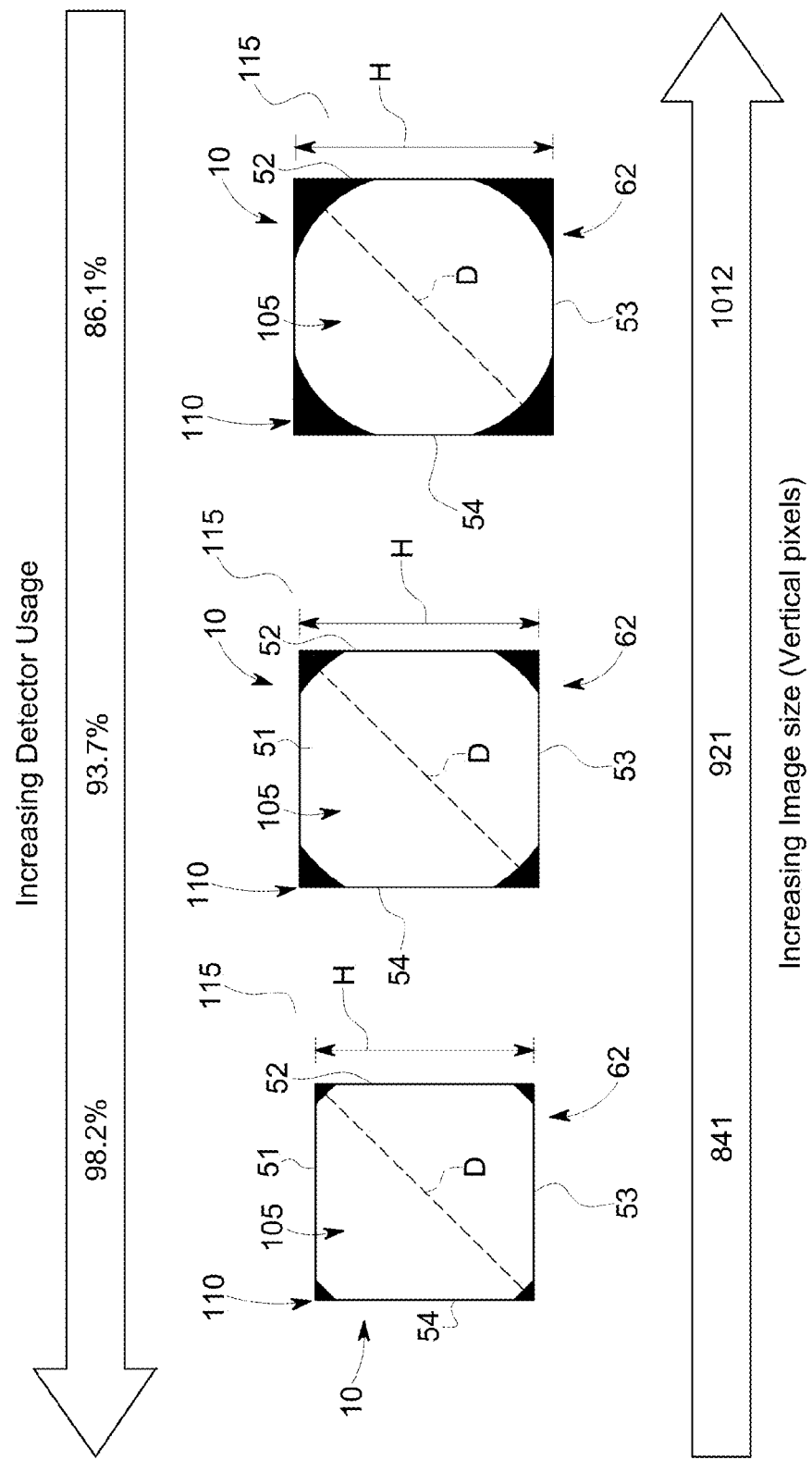
FIG. 17 shows a view of some embodiments of the image on a display device.

Additionally, where a border 63 (as described above) separates two substantially perpendicular edges (e.g., 91 and 92, 92 and 93, 93, and 94, and/or 91 and 94) of the aperture 50, the borders can be any suitable shape that allows the collimator to function as described herein. By way of example, FIGS. 14-16 illustrate additional embodiments in which the image 10 has the shape of a squircle, wherein the image 10 in FIG. 14 is predominantly square shaped, the image 10 in FIG. 16 is predominantly circular in shaped, and the image 10 in FIG. 15 has a shape between those shown in FIGS. 14 and 16.

Where the collimator 30 shields a portion of the X-ray detector 25 (e.g. one or more of the detector's corners 55), the aperture can leave any suitable amount of the receptor area 62 exposed to X-rays from the X-ray source 20. This configuration allows an image 10 taken with the collimator to be rotated on a display device without being resized or reshaped. In some cases, the collimator allows less than an amount selected from about 100%, about 98.5%, about 94%, about 90%, about 87%, or about 80% of the detector's receptor area to be exposed to X-rays from the X-ray source. In other cases, the collimator allows more than an amount selected from about 78.5%, about 79%, about 80%, about 82%, about 84%, and about 85% of the detector's receptor area to be exposed to X-rays from the X-ray source. In yet other cases, the aperture can allow any suitable combination or sub-range of these amounts of the detector's receptor area to be exposed to X-rays. For example, FIG. 17 shows some embodiments in which the collimator (not shown) allows (from left to right) about 98.2%, about 93.7%, and about 86.1% of the detector's receptor area 62 to be exposed to X-rays (exposed area 105) and in which about 1.8%, about 6.4%, and about 17.9% of the receptor area 62, respectively is shielded by the collimator (unexposed area 110). In other words, FIG. 17 shows the trade-off between an on-screen image size and the detector utilization. The more square the image is, the smaller it has to appear on the screen in order to be rotatable. In some embodiments of the squircles described herein, the geometry could range between a full square (100% of the detector utilized) and a full circle (78.5% utilization).

Returning to the method 150 in FIG. 2, after an image 10 has been taken of an object (as shown at 160), the method continues at box 165, where the collimated X-ray image is shown on a display device (e.g., a screen, monitor, tablet/handheld device, etc.). The image can take up any suitable amount of the display device's display area that allows the entire image to be viewed as it is rotated at least 45 degrees about its center, without being resized or reshaped.

The height H (e.g., the distance between the first 51 and third 53 or second 52 and fourth 54 edges) of the image 10 can be any height that allows the entire image to be rotated on the display device 115 without the image being resized or reshaped. In some embodiments, the height H is greater than an amount selected from about 71.6%, about 75%, about 80%, or about 82.5% of the narrower of the width and length of the display area. In other embodiments, the height H of the image is less than an amount selected from about 100%, about 98%, about 95%, and about 90% of the height of the display area. In yet other embodiments, the image's height H falls between any suitable combination or sub-range of these amounts. For example, FIG. 17 shows that where the display device 115 comprises an HD display device (e.g., a device having a pixel resolution of 1080 pixels by 1920 pixels), the image 10 can have a height of about 841 pixels (where about 98.2% of the detector's receptor area is exposed), about 921 pixels (where about 93.7% of the detector's receptor area 62 is exposed), or about 1012 pixels (where about 78.5% of the detector's receptor area is exposed to X-rays).

Because some embodiments of the aperture 50 can have any shape between a full circle (e.g., in which about 78.5% of a square detector are is utilized) and a true square (e.g., in which about 100% of the square detector is utilized), the widest portion D (e.g., a diagonal measurement) of the collimated image can be any length that allows the entire image to be rotated on the display device 115 without the image being resized or reshaped. In some embodiments, the widest portion D of the image is less than an amount selected from about 100%, about 99%, and about 96% of the width or length of the display's display area, whichever is narrower. In other embodiments, the widest portion D of the image is greater than an amount selected from about 85%, about 90%, and about 95% of the width or length of the display area, whichever is narrower. In still other embodiments, the widest portion D of the image can be between any suitable combination or sub-range of these amounts.

In some instances, the shape of the aperture 50 helps provide a desired balance between the on-screen image size of the image 10 and detector utilization. By way of illustration, FIG. 17 shows that, in some cases, the more square the image 10 is, the smaller it has to be on the display device 115 in order to be entirely seen as it is rotated. In contrast, where the aperture has borders 63 that are arcs of a true circle, thereby providing a squircle image, the entire squircle can be rotated on the display device without clipping any part of the image and without rescaling the shape as long as the true circle could be fully displayed on the device.

Figure 18:
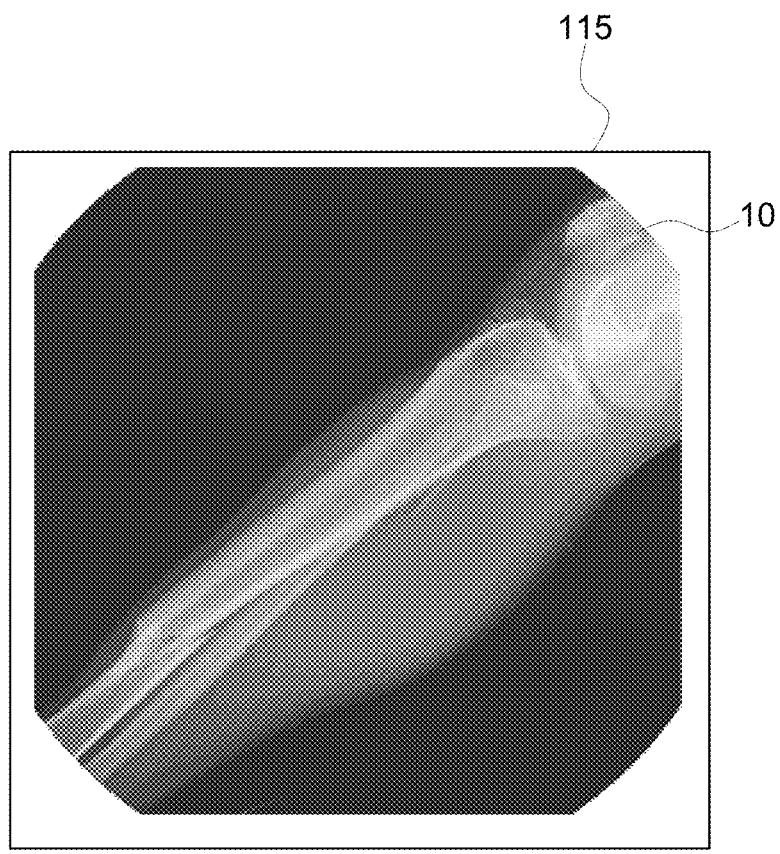
FIGS. 18-20 show some embodiments of the collimated image being rotated.
Figure 19:
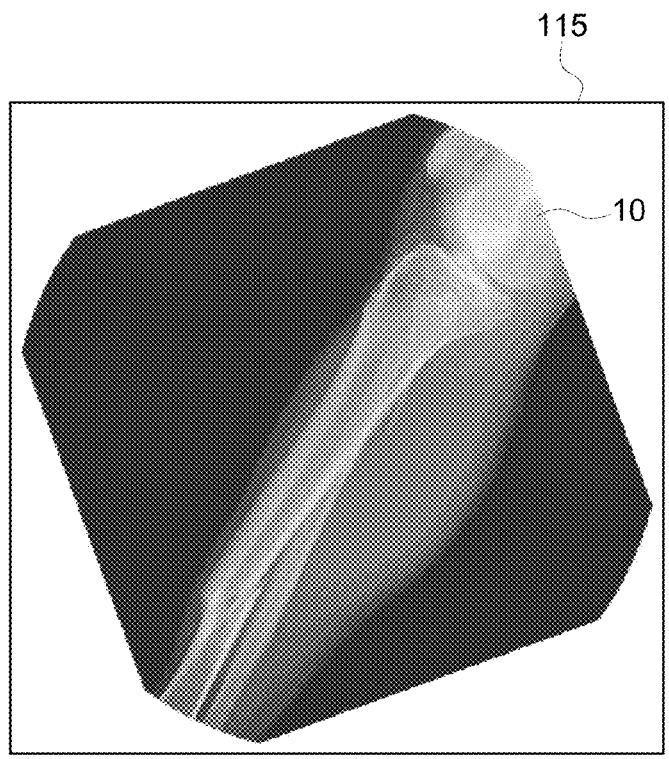
Figure 20:
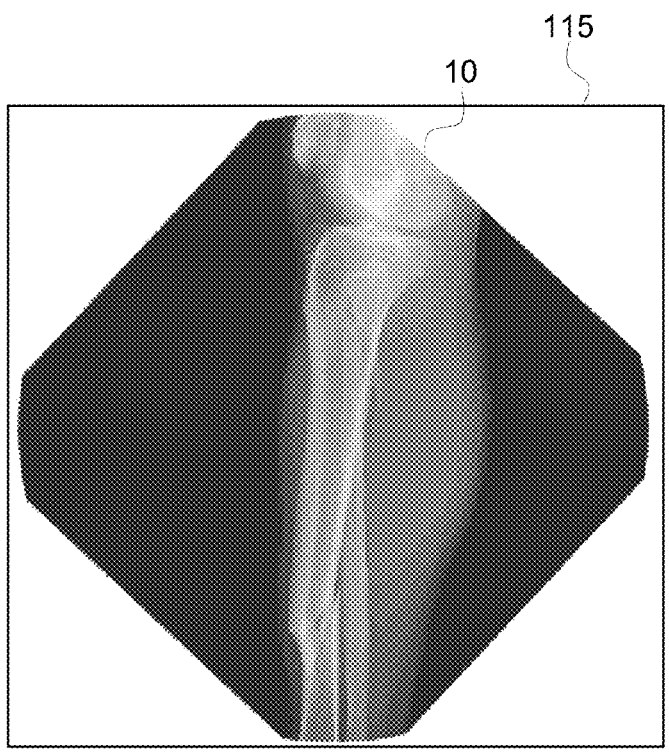
Figure 21:
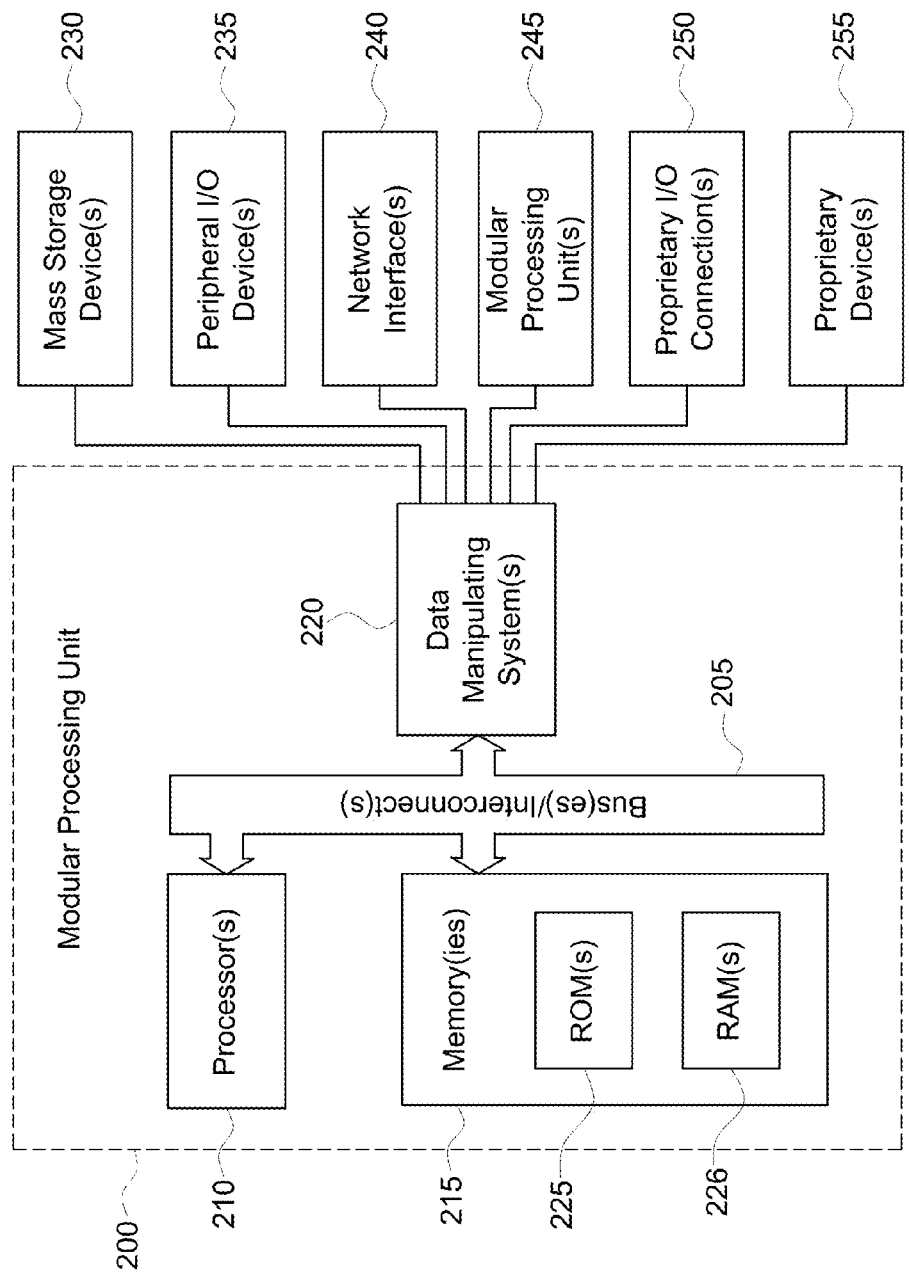
FIGS. 21-22 show some embodiments of systems that can provide a suitable computing environment for some embodiments of the described methods.

Returning to FIG. 2, the method 150 continues at box 165 where the collimated image is optionally shown on a display device 115. At box 170, the method 150 optionally includes a process of rotating the image clockwise and/or counter-clockwise. FIGS. 18 through 20 show successive views of the image 10 being rotated counter-clockwise on a display device 115. As the image 10 is rotated, the entire image can be viewed on the display device 115, without any resizing or reshaping of the image. Thus, in some embodiments, the exposed area of the live image (and not the processed image) can be substantially equal to the displayed area.

Where the collimated X-ray images 10 are shown, rotated, or otherwise manipulated on a display device 115, the display device can be used with any suitable computing environment. FIG. 21 describes some embodiments of one exemplary computing environment. These embodiments can include one or more processing units in a variety of customizable enterprise configurations, including in a networked or combination configuration. These embodiments can include one or more computer readable media, wherein each medium may be configured to include or includes thereon data or computer executable instructions for manipulating data. The computer executable instructions can include data structures, objects, programs, routines, or other program modules that may be accessed by one or more processors, such as one associated with a general-purpose modular processing unit capable of performing various different functions or one associated with a special-purpose modular processing unit capable of performing a limited number of functions.

Computer executable instructions cause the one or more processors of the enterprise to perform a particular function or group of functions and are examples of program code means for implementing steps for methods of processing. Furthermore, a particular sequence of the executable instructions provides an example of corresponding acts that may be used to implement such steps.

Examples of computer readable media (including non-transitory computer readable media) include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), any solid state storage device (e.g., flash memory, smart media, etc.), or any other device or component capable of providing data or executable instructions that may be accessed by a processing unit.

With reference to FIG. 21, a representative enterprise includes modular processing unit 200, which may be used as a general-purpose or special-purpose processing unit. For example, modular processing unit 200 may be employed alone or with one or more similar modular processing units as a personal computer, a notebook computer, a personal digital assistant ("PDA") or other hand-held device, a workstation, a minicomputer, a mainframe, a supercomputer, a multi-processor system, a network computer, a processor-based consumer device, a cellular phone, a smart appliance or device, a control system, or the like. Using multiple processing units in the same enterprise provides increased processing capabilities. For example, each processing unit of an enterprise can be dedicated to a particular task or can jointly participate in distributed processing.

In FIG. 21, the modular processing unit 200 includes one or more buses and/or interconnects 205, which may be configured to connect various components thereof and enables data to be exchanged between two or more components. The bus(es)/interconnect(s) 205 may include one of a variety of bus structures, including a memory bus, a peripheral bus, or a local bus that uses any of a variety of bus architectures. Typical components connected by the bus(es)/interconnect(s) 205 include one or more processors 210 and one or more memories 215. Other components may be selectively connected to the bus(es)/interconnect(s) 205 through the use of logic, one or more systems, one or more subsystems and/or one or more I/O interfaces, hereafter referred to as data manipulating system(s) 220. Moreover, other components may be externally connected to the bus(es)/interconnect(s) 205 through the use of logic, one or more systems, one or more subsystems and/or one or more I/O interfaces, and/or may function as logic, one or more systems, one or more subsystems, and/or one or more I/O interfaces, such as one or more modular processing unit(s) 245 and/or proprietary device(s) 255. Examples of I/O interfaces include one or more mass storage device interfaces, one or more input interfaces, one or more output interfaces, and the like. Accordingly, embodiments of the described systems and methods embrace the ability to use one or more I/O interfaces and/or the ability to change the usability of a product based on the logic or other data manipulating system employed.

The logic may be tied to an interface, part of a system, subsystem and/or be used to perform a specific task. Accordingly, the logic or other data manipulating system may allow, for example, for IEEE1394 (firewire), wherein the logic or other data manipulating system is an I/O interface. Alternatively or additionally, logic or another data manipulating system may be used that allows a modular processing unit to be tied into another external system or subsystem. For example, an external system or subsystem that may or may not include a special I/O connection. Alternatively or additionally, logic or another data manipulating system may be used wherein no external I/O is associated with the logic. Embodiments of the described systems and methods also embrace the use of specialty logic, such as for ECUs for vehicles, hydraulic control systems, etc. and/or logic that informs a processor how to control a specific piece of hardware. Moreover, those skilled in the art will appreciate that embodiments of the described systems and methods embrace a plethora of different systems and/or configurations that utilize logic, systems, subsystems and/or I/O interfaces.

As provided above, embodiments of the described systems and methods embrace the ability to use one or more I/O interfaces and/or the ability to change the usability of a product based on the logic or other data manipulating system employed. For example, where a modular processing unit is part of a personal computing system that includes one or more I/O interfaces and logic designed for use as a desktop computer, the logic or other data manipulating system can be changed to include flash memory or logic to perform audio encoding for a music station that wants to take analog audio via two standard RCAs and broadcast them to an IP address. Accordingly, the modular processing unit may be part of a system that is used as an appliance rather than a computer system due to a modification made to the data manipulating system(s) (e.g., logic, system, subsystem, I/O interface(s), etc.) on the back plane of the modular processing unit. Thus, a modification of the data manipulating system(s) on the back plane can change the application of the modular processing unit. Accordingly, embodiments of the described systems and methods embrace very adaptable modular processing units.

As provided above, processing unit 200 includes one or more processors 210, such as a central processor (or CPU) and optionally one or more other processors designed to perform a particular function or task. It is typically the processor 210 that executes the instructions provided on computer readable media, such as on the memory(ies) 215, a magnetic hard disk, a removable magnetic disk, a magnetic cassette, an optical disk, or from a communication connection, which may also be viewed as a computer readable medium.

The memory(ies) 215 includes one or more computer readable media that may be configured to include or includes thereon data or instructions for manipulating data, and may be accessed by the processor(s) 210 through the bus(es)/interconnect(s) 205. The memory(ies) 215 may include, for example, ROM(s) 225, used to permanently store information, and/or RAM(s) 226, used to temporarily store information. The ROM(s) 225 may include a basic input/output system ("BIOS") having one or more routines that are used to establish communication, such as during start-up of the modular processing unit 200. During operation, the RAM(s) 226 may include one or more program modules, such as one or more operating systems, application programs, and/or program data.

As illustrated, at least some embodiments of the described systems and methods embrace a non-peripheral encasement, which provides a more robust processing unit that enables use of the unit in a variety of different applications. In FIG. 21, one or more mass storage device interfaces (illustrated as data manipulating system(s) 220) may be used to connect one or more mass storage devices 230 to the bus(es)/interconnect(s) 205. The mass storage devices 230 are peripheral to the modular processing unit 200 and allow the modular processing unit 200 to retain large amounts of data. Examples of mass storage devices include hard disk drives, magnetic disk drives, tape drives and optical disk drives.

A mass storage device 230 may read from and/or write to a magnetic hard disk, a removable magnetic disk, a magnetic cassette, an optical disk, or another computer readable medium. The mass storage devices 230 and their corresponding computer readable media provide nonvolatile storage of data and/or executable instructions that may include one or more program modules, such as an operating system, one or more application programs, other program modules, or program data. Such executable instructions are examples of program code means for implementing steps for methods disclosed herein.

The data manipulating system(s) 220 may be employed to enable data and/or instructions to be exchanged with the modular processing unit 200 through one or more corresponding peripheral I/O devices 235. Examples of the peripheral I/O devices 235 include input devices such as a keyboard and/or alternate input devices, such as a mouse, trackball, light pen, stylus, or other pointing device, a microphone, a joystick, a game pad, a satellite dish, a scanner, a camcorder, a digital camera, a sensor, and the like, and/or output devices such as a display device 115 (e.g., a monitor or display screen), a speaker, a printer, a control system, and the like. Similarly, examples of the data manipulating system(s) 220 coupled with specialized logic that may be used to connect the peripheral I/O devices 235 to the bus(es)/interconnect(s) 205 include a serial port, a parallel port, a game port, a universal serial bus ("USB"), a firewire (IEEE 1394), a wireless receiver, a video adapter, an audio adapter, a parallel port, a wireless transmitter, any parallel or serialized I/O peripherals or another interface.

The data manipulating system(s) 220 enable an exchange of information across one or more network interfaces 240. Examples of the network interfaces 240 include a connection that enables information to be exchanged between processing units, a network adapter for connection to a local area network ("LAN") or a modem, a wireless link, or another adapter for connection to a wide area network ("WAN"), such as the Internet. The network interface 240 may be incorporated with or peripheral to modular processing unit 200, and may be associated with a LAN, a wireless network, a WAN and/or any 260 connection (see FIG. 22) between processing units.

The data manipulating system(s) 220 enables the modular processing unit 200 to exchange information with one or more other local or remote modular processing units 245 or computer devices. A connection between modular processing unit 200 and modular processing unit 245 may include hardwired and/or wireless links. Accordingly, embodiments of the described systems and methods embrace direct bus-to-bus connections. This enables the creation of a large bus system. It also eliminates hacking as currently known due to direct bus-to-bus connections of an enterprise. Furthermore, the data manipulating system(s) 220 enable the modular processing unit 200 to exchange information with one or more proprietary I/O connections 250 and/or one or more proprietary devices 255.

Program modules or portions thereof that are accessible to the processing unit may be stored in a remote memory storage device. Furthermore, in a networked system or combined configuration, the modular processing unit 200 may participate in a distributed computing environment where functions or tasks are performed by a plurality of processing units. Alternatively, each processing unit of a combined configuration/enterprise may be dedicated to a particular task. Thus, for example, one processing unit of an enterprise may be dedicated to video data, thereby replacing a traditional video card, and provides increased processing capabilities for performing such tasks over traditional techniques.

Figure 22:
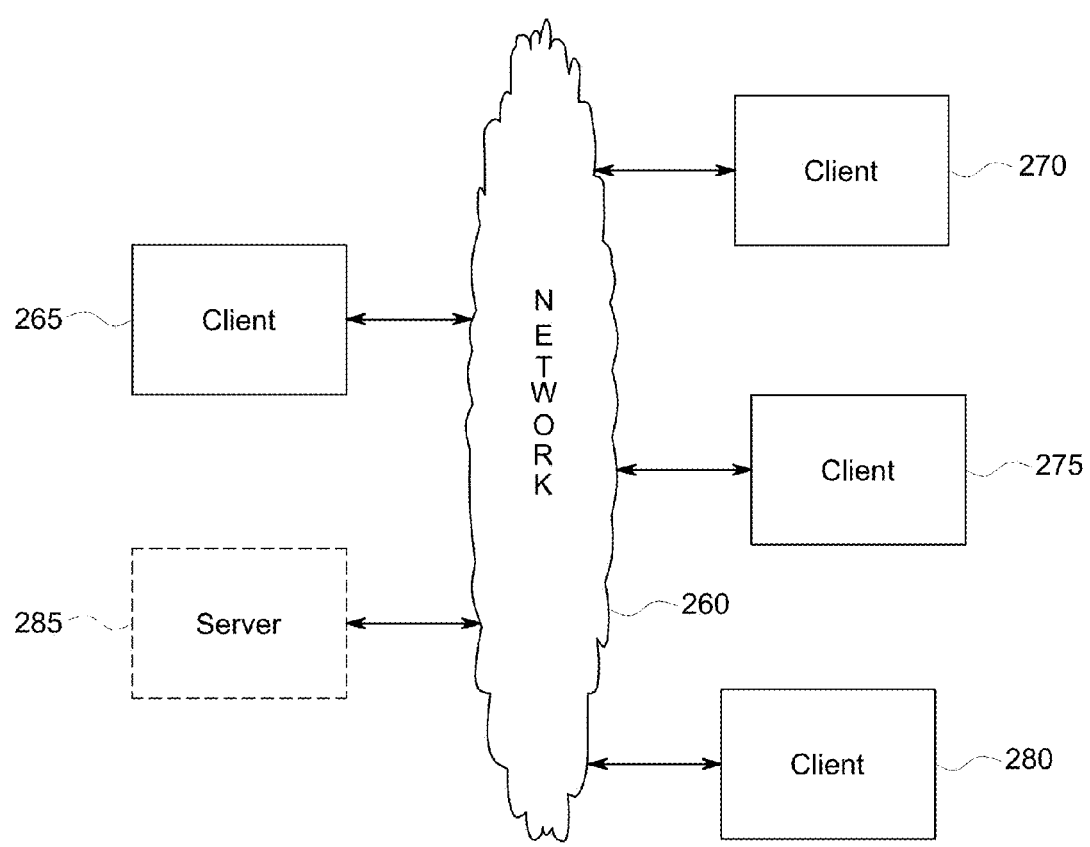

While those skilled in the art will appreciate that the described systems and methods may be practiced in networked computing environments with many types of computer system configurations, FIG. 22 represents an embodiment of a portion of the described systems in a networked environment that includes clients (265, 270, 275, 280, etc.) connected to a server 285 via a network 260. While FIG. 22 illustrates an embodiment that includes four clients connected to the network, alternative embodiments include one client connected to a network or many clients connected to a network. Moreover, embodiments in accordance with the described systems and methods also include a multitude of clients throughout the world connected to a network, where the network is a wide area network, such as the Internet. Accordingly, in some embodiments, the described systems and methods can allow a collimated image 10 to be taken in a first location and a user (e.g., a radiologist, technician, physician, etc.) to view, rotate, and otherwise manipulate the image from a second location.

As previously mentioned, the described systems and methods can be modified in any suitable manner. In one example, where computer software is used to display the described collimated images 10 on a display device, the software can be used to clean up the images in any suitable manner. For instance, the software can be used to remove shadows, fuzzy lines, or to otherwise sharpen the image's edges.

The described systems and methods for displaying collimated X-ray images 10 have several useful features. First, unlike some conventional methods that use a collimator to shield a relatively large amount of the detector's receptor area, some embodiments of the described systems and methods shield a relatively small amount of the detector's receptor area (as discussed above). Thus, some conventional methods are limited to using a collimator having a circular aperture with a circumference that falls completely within all of the perimeters of a four-sided flat panel detector. As a result, a relatively large amount of the receptor area in such conventional methods is not used. Second, while some conventional methods shrink an X-ray image as the image is rotated, some embodiments of the described systems and methods allow the image to be relatively large with respect to the display's display area and to be rotated while maintaining a substantially constant size and shape. And third, unlike some conventional methods for displaying an X-ray image that only show a small square image that can be rotated without being resized or reshaped, some embodiments of the described methods allow the described images 10 to use a relatively large amount of the display's display area without needing any resizing or reshaping. Thus, users of the described systems can see better detail on the collimated images than may be obtained through some other conventional methods.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples and embodiments, in all respects, are meant to be illustrative only and should not be construed to be limiting in any manner.

The invention claimed is:

1. An X-ray imaging device, comprising:
an X-ray source;
a square or rectangular X-ray detector; and
a collimator comprising an X-ray attenuating material with an aperture therein, the collimator configured to produce an X-ray image with a superellipse shape having a first substantially straight edge and a second substantially straight edge running substantially perpendicular to the first edge, wherein the first and second edges do not physically intersect with each other at 90 degrees.

2. The device of claim 1, wherein the image further comprises a third substantially straight edge and a fourth substantially straight edge running substantially perpendicular to the third edge, and wherein third and fourth edges to not physically intersect with each other at 90 degrees.

3. The device of claim 2, wherein the first and third edges do not physically intersect with each other at 90 degrees, and wherein the second and fourth edges do not physically intersect with each other at 90 degrees.

4. The device of claim 2, wherein the image further comprises a rounded or curved border between the first and second edges, between the second and fourth edges, between the third and fourth edges, or between the third and first edges.

5. The device of claim 2, wherein the image is configured to be displayed on a square or rectangular display and the entire X-ray image can be rotated and viewed on the display without resizing or reshaping the image.

* * * * *